(12) United States Patent
Smith et al.

(10) Patent No.: US 11,793,242 B2
(45) Date of Patent: *Oct. 24, 2023

(54) ADAPTOR FOR USE WITH NON-CYLINDRICAL VAPOR PRODUCTS

(71) Applicant: RAI STRATEGIC HOLDINGS, INC., Winston-Salem, NC (US)

(72) Inventors: Jeffrey Sean Smith, Winston-Salem, NC (US); Robert Underly, Pfafftown, NC (US); Jason M. Short, Winston-Salem, NC (US); Cassidy McMahan, Pfafftown, NC (US); Yi-Ping Chang, Greensboro, NC (US); Bradley Brown, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 127 days.

This patent is subject to a terminal disclaimer.

(21) Appl. No.: 17/526,452

(22) Filed: Nov. 15, 2021

(65) Prior Publication Data

US 2022/0071307 A1 Mar. 10, 2022

Related U.S. Application Data

(63) Continuation of application No. 16/827,445, filed on Mar. 23, 2020, now Pat. No. 11,191,306, which is a
(Continued)

(51) Int. Cl.
*A24F 40/80* (2020.01)
*A24D 3/17* (2020.01)
(Continued)

(52) U.S. Cl.
CPC ............... *A24F 40/80* (2020.01); *A24D 3/17* (2020.01); *A24D 3/18* (2013.01); *G01D 11/24* (2013.01); *G01N 33/0009* (2013.01)

(58) Field of Classification Search
CPC ...... G01N 33/0009; G01N 2035/00306; A24F 40/40; A24F 40/80; G01D 11/24
See application file for complete search history.

(56) References Cited

U.S. PATENT DOCUMENTS

| 2,974,669 A | 3/1961 | Ellis |
| 4,627,448 A | 12/1986 | Kamm et al. |

(Continued)

FOREIGN PATENT DOCUMENTS

| CN | 104783331 A1 | 7/2015 |
| FR | 2879746 A1 | 6/2006 |

(Continued)

OTHER PUBLICATIONS

International Search Report and Written Opinion of the ISA/EP in PCT/US2020/031329, dated Aug. 6, 2020, 14 pages.

(Continued)

*Primary Examiner* — Benjamin R Schmitt
(74) *Attorney, Agent, or Firm* — BURR & FORMAN LLP

(57) ABSTRACT

A system for testing a vapor product with a mouthpiece that has a non-circular cross section includes an adaptor coupled to a neck portion of a filter pad holder. The adaptor includes a nose to receive the neck portion and an adaptor body coupled to the nose. An opening is defined by the adaptor body and the nose, the opening extending through the adaptor body and the nose and configured to receive the neck portion. A sealing member is configured to be received by the adaptor and the filter pad holder. The sealing member includes a sealing member nose configured to be received by the neck portion, and a sealing member body coupled to the sealing member nose and configured to be received by the opening. The sealing member body defines an orifice, the orifice extending through the sealing member body.

20 Claims, 7 Drawing Sheets

Related U.S. Application Data continuation-in-part of application No. 16/408,336, filed on May 9, 2019, now Pat. No. 11,119,083.

(51) Int. Cl.
  *A24D 3/18* (2006.01)
  *G01N 33/00* (2006.01)
  *G01D 11/24* (2006.01)

(56) References Cited

U.S. PATENT DOCUMENTS

| | | |
|---|---|---|
| 4,714,082 A | 12/1987 | Banerjee et al. |
| 4,756,318 A | 7/1988 | Clearman et al. |
| 4,771,795 A | 9/1988 | White et al. |
| 4,793,365 A | 12/1988 | Sensabaugh et al. |
| 4,917,128 A | 4/1990 | Clearman et al. |
| 4,922,901 A | 5/1990 | Brooks et al. |
| 4,961,438 A | 10/1990 | Korte |
| 4,966,171 A | 10/1990 | Serrano et al. |
| 4,969,476 A | 11/1990 | Bale et al. |
| 4,991,606 A | 2/1991 | Serrano et al. |
| 5,020,548 A | 6/1991 | Farrier et al. |
| 5,033,483 A | 7/1991 | Clearman et al. |
| 5,040,551 A | 8/1991 | Schlatter et al. |
| 5,050,621 A | 9/1991 | Creighton et al. |
| 5,060,671 A | 10/1991 | Counts et al. |
| 5,065,776 A | 11/1991 | Lawson et al. |
| 5,076,296 A | 12/1991 | Nystrom et al. |
| 5,076,297 A | 12/1991 | Farrier et al. |
| 5,099,861 A | 3/1992 | Clearman et al. |
| 5,105,835 A | 4/1992 | Drewett et al. |
| 5,105,837 A | 4/1992 | Barnes et al. |
| 5,115,820 A | 5/1992 | Hauser et al. |
| 5,148,821 A | 9/1992 | Best et al. |
| 5,159,940 A | 11/1992 | Hayward et al. |
| 5,178,167 A | 1/1993 | Riggs et al. |
| 5,183,062 A | 2/1993 | Clearman et al. |
| 5,211,684 A | 5/1993 | Shannon et al. |
| 5,240,014 A | 8/1993 | Deevi et al. |
| 5,240,016 A | 8/1993 | Nichols et al. |
| 5,345,955 A | 9/1994 | Clearman et al. |
| 5,388,594 A | 2/1995 | Counts et al. |
| 5,551,451 A | 9/1996 | Riggs et al. |
| 5,595,577 A | 1/1997 | Bensalem et al. |
| 5,726,421 A | 3/1998 | Fleischhauer et al. |
| 5,819,751 A | 10/1998 | Barnes et al. |
| 6,089,857 A | 7/2000 | Matsuura et al. |
| 6,095,152 A | 8/2000 | Beven et al. |
| 6,578,584 B1 | 6/2003 | Beven et al. |
| 6,730,832 B1 | 5/2004 | Dominguez |
| 7,290,549 B2 | 11/2007 | Banerjee et al. |
| 8,079,371 B2 | 12/2011 | Robinson et al. |
| 8,402,976 B2 | 3/2013 | Fernando et al. |
| 8,424,538 B2 | 4/2013 | Thomas et al. |
| 8,464,726 B2 | 6/2013 | Sebastian et al. |
| 8,469,035 B2 | 6/2013 | Banerjee et al. |
| 8,617,263 B2 | 12/2013 | Banerjee et al. |
| 8,851,081 B2 | 10/2014 | Fernando et al. |
| 9,016,274 B1 | 4/2015 | White |
| 9,078,474 B2 | 7/2015 | Thompson |
| 9,149,072 B2 | 10/2015 | Conner et al. |
| 9,214,268 B2 | 12/2015 | Difonzo et al. |
| 9,220,301 B2 | 12/2015 | Banerjee et al. |
| 9,301,546 B2 | 4/2016 | Thomas et al. |
| 9,332,784 B2 | 5/2016 | Banerjee et al. |
| 9,345,268 B2 | 5/2016 | Stone et al. |
| 9,439,453 B2 | 9/2016 | Conner et al. |
| 9,486,013 B2 | 11/2016 | Sebastian et al. |
| 9,788,571 B2 | 10/2017 | Conner et al. |
| 9,814,268 B2 | 11/2017 | Robinson et al. |
| 9,839,241 B2 | 12/2017 | Davidson et al. |
| 9,933,790 B2 | 4/2018 | Blackley |
| 2004/0031497 A1 | 2/2004 | Likness et al. |
| 2004/0177674 A1 | 9/2004 | Read et al. |
| 2008/0257368 A1 | 10/2008 | Wilson et al. |
| 2011/0265806 A1 | 11/2011 | Alarcon et al. |
| 2013/0220315 A1 | 8/2013 | Conley et al. |
| 2013/0255702 A1 | 10/2013 | Griffith et al. |
| 2013/0255703 A1 | 10/2013 | Banerjee et al. |
| 2013/0284192 A1 | 10/2013 | Peleg et al. |
| 2014/0000638 A1 | 1/2014 | Sebastian et al. |
| 2014/0060554 A1 | 3/2014 | Collett et al. |
| 2014/0096781 A1 | 4/2014 | Sears et al. |
| 2014/0096782 A1 | 4/2014 | Ampolini et al. |
| 2015/0053217 A1 | 2/2015 | Steingraber et al. |
| 2015/0059780 A1 | 3/2015 | Davis et al. |
| 2015/0157052 A1 | 6/2015 | Ademe et al. |
| 2015/0245654 A1 | 9/2015 | Memari et al. |
| 2015/0335070 A1 | 11/2015 | Sears et al. |
| 2016/0002484 A1 | 1/2016 | Geisen et al. |
| 2016/0157524 A1 | 6/2016 | Bowen et al. |
| 2016/0219938 A1 | 8/2016 | Mamoun et al. |
| 2016/0302484 A1 | 10/2016 | Gupta et al. |
| 2017/0000188 A1 | 1/2017 | Nordskog et al. |
| 2017/0055576 A1 | 3/2017 | Beeson et al. |
| 2017/0065000 A1 | 3/2017 | Sears et al. |
| 2017/0164654 A1 | 6/2017 | Ademe |
| 2017/0238607 A1 | 8/2017 | Nordskog |
| 2017/0340008 A1 | 11/2017 | Sebastian et al. |
| 2018/0289074 A1 | 10/2018 | Tremblay |
| 2019/0082737 A1 | 3/2019 | Smith et al. |
| 2019/0087302 A1 | 3/2019 | Smith et al. |
| 2019/0255266 A1 | 8/2019 | Henry et al. |

FOREIGN PATENT DOCUMENTS

| | | |
|---|---|---|
| WO | WO-98/46093 A1 | 10/1998 |
| WO | WO-02/098245 A1 | 12/2002 |
| WO | WO-2017/023589 A1 | 2/2017 |
| WO | WO-2017/027673 A1 | 2/2017 |

OTHER PUBLICATIONS

Notice of Allowance in U.S. Appl. No. 15/710,681, dated Aug. 28, 2020, 8 pages.
Final Office Action in U.S. Appl. No. 15/892,151, dated Nov. 24, 2020, 25 pages.
Non-Final Office Action in U.S. Appl. No. 16/131,785, dated Dec. 9, 2020, 16 pages.
Non-Final Office Action in U.S. Appl. No. 15/892,151, dated Jun. 1, 2020, 22 pages.
Non-Final Office Action in U.S. Appl. No. 16/131,785, dated Jul. 10, 2020, 12 pages.
International Search Report and Written Opinion in PCT/US2018/051543, dated Dec. 20, 2018, 22 pages.
Non-Final Office Action in U.S. Appl. No. 15/710,681, dated Jun. 27, 2019, 11 pages.
Non-Final Office Action in U.S. Appl. No. 15/892,151, dated Oct. 10, 2019, 20 pages.
International Search Report and Written Opinion in PCT/US2019/050047, dated Dec. 12, 2019, 15 pages.
Final Office Action in U.S. Appl. No. 15/710,681, dated Jan. 6, 2020, 15 pages.
Non-Final Office Action for U.S. Appl. No. 15/892,151, dated Jun. 11, 2021.

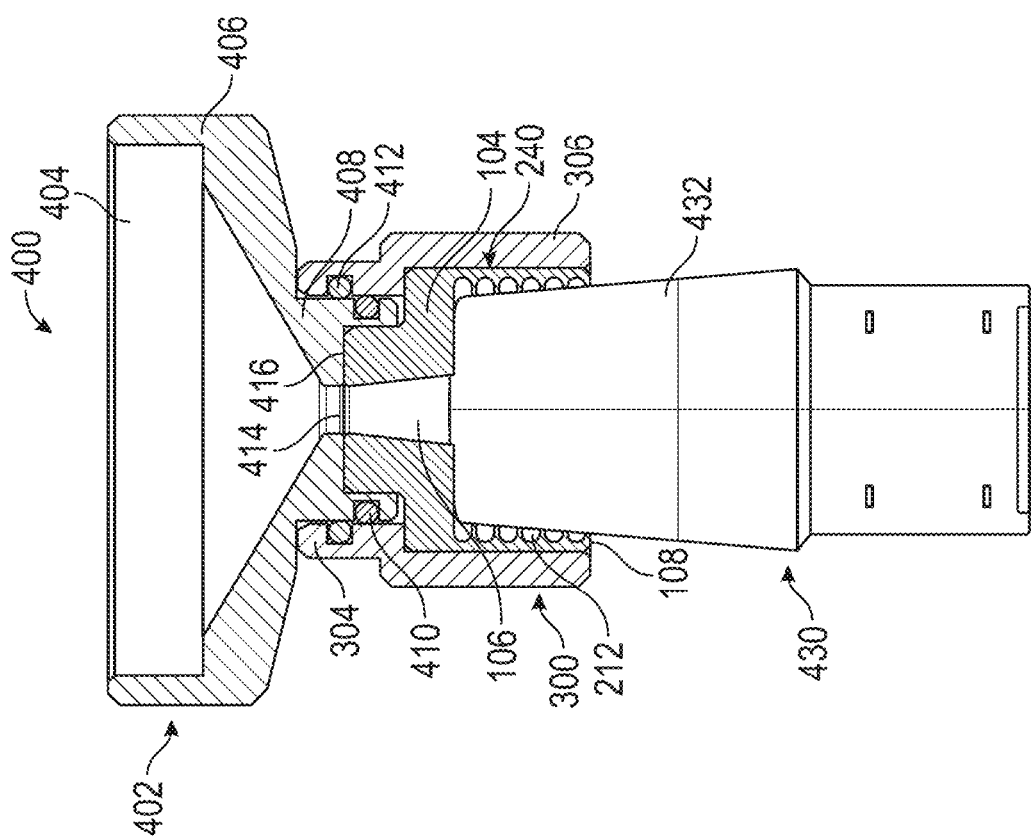
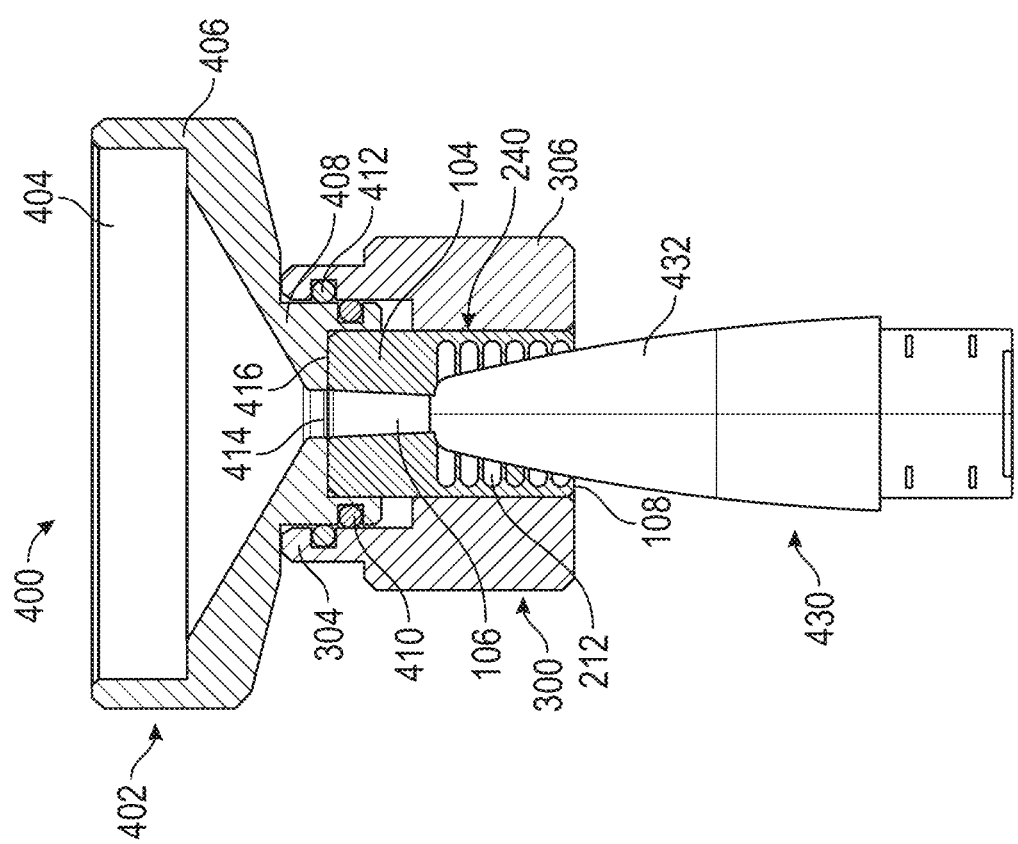

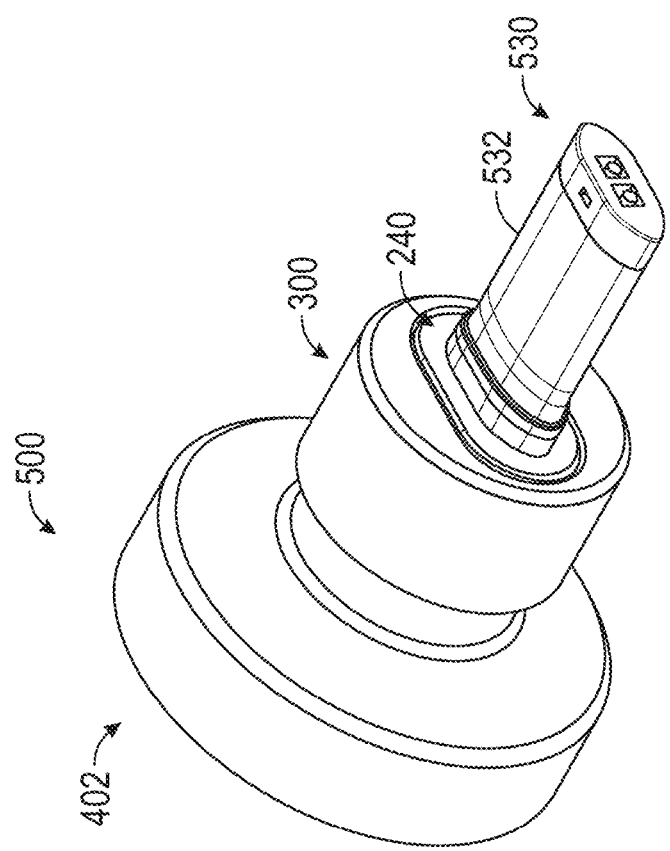
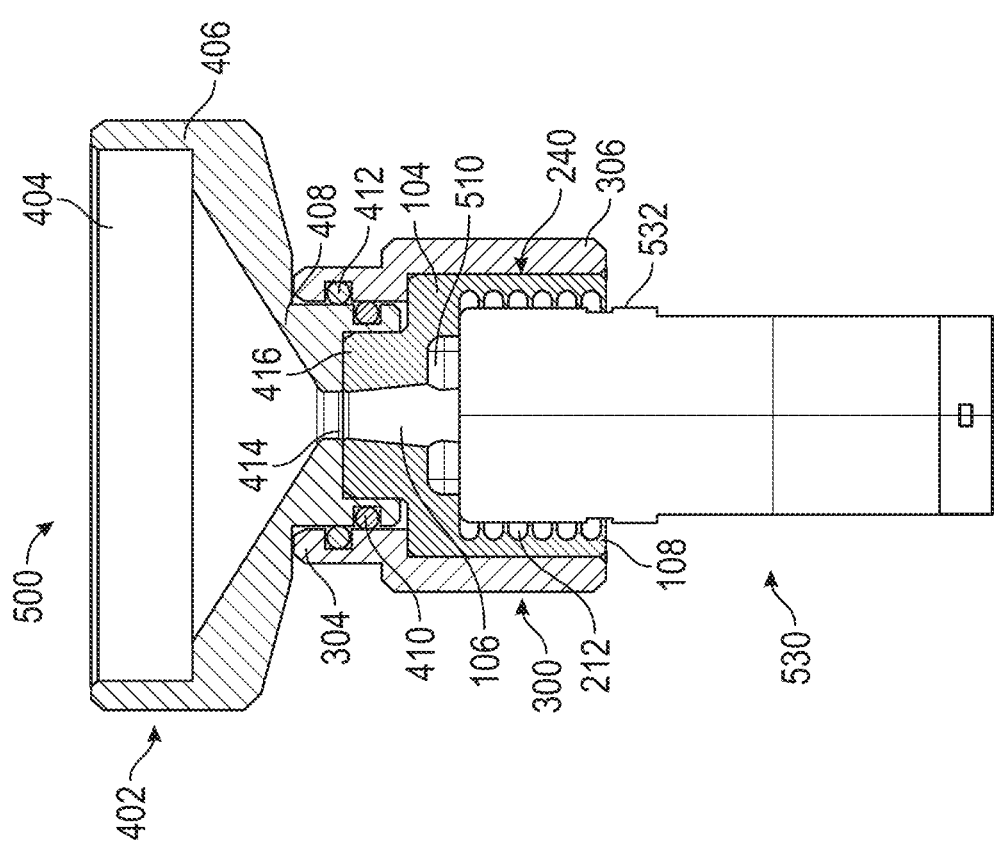
FIG. 5C
FIG. 5B

ADAPTOR FOR USE WITH NON-CYLINDRICAL VAPOR PRODUCTS

CROSS-REFERENCE TO RELATED APPLICATIONS

The present application is a continuation of U.S. patent application Ser. No. 16/827,445, filed on Mar. 23, 2020, which is a continuation-in-part of U.S. patent application Ser. No. 16/408,336, filed on May 9, 2019, now U.S. Pat. No. 11,119,083, the contents of which are incorporated herein by reference in their entireties.

TECHNICAL FIELD

The present disclosure relates to adaptors for testing vapor products. More particularly, the present disclosure relates to adaptors for testing vapor products that include mouthpieces with a non-circular cross-section.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. For example, various alternative smoking articles, aerosol delivery devices and heat generating sources are set forth in the background art described in U.S. Pat. App. Pub. No. 2013/0255702 to Griffith Jr. et al., U.S. Pat. App. Pub. No. 2014/0000638 to Sebastian et al., U.S. Pat. No. 5,060,671 to Counts et al.; U.S. Pat. No. 9,016,274 to White; U.S. Pat. No. 9,078,474 to Thompson; U.S. Pat. App. Pub. No. 2014/0060554 to Collett et al., U.S. Pat. App. Pub. No. 2014/0096781 to Sears et al., U.S. patent application Ser. No. 13/826,929 to Ampolini et al., filed Mar. 14, 2013, and U.S. patent application Ser. No. 14/011,992 to Davis et al., filed Aug. 28, 2013, which are incorporated herein by reference in their entireties. Other various embodiments of products and heating configurations are described in the background sections of U.S. Pat. No. 5,388,594 to Counts et al. and U.S. Pat. No. 8,079,371 to Robinson et al., which are incorporated by reference in their entireties.

Popular electronic or electrically powered smoking articles (e.g., electronic cigarettes, E-cigarettes, etc.) (referred to herein collectively as "vapor products") often include a liquid storage component for storing aerosol precursor material (e.g., aerosol forming agent, liquid smoke, etc.), a vaporizing chamber with a heating coil attached for the aerosol precursor material to become vaporized therein, and a battery to power the device. The heating coil material typically includes a nickel/chromium wire, a titanium wire, nichrome wire, or similar alloy wires. The aerosol precursor material typically includes a mixture of propylene glycol, glycerin, nicotine, water and flavoring. Various electronic smoking articles have a single device which houses both the heating element and the aerosol precursor material in one unit, commonly referred to as a cartomizer.

Certain tobacco products that have employed electrical energy to produce heat for smoke or aerosol formation. In particular, certain products that have been referred to as electronic cigarette products or electronic smoking articles have been commercially available throughout the world. Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; GREEN SMOKE® by Green Smoke Inc. USA; GREENARETTE™ by Greenarette LLC; HALLIGAN™, HENDU™ JET™, MAXXQ™ PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC and VUSE® by R. J. Reynolds Vapor Company. Yet other electrically powered aerosol delivery devices, and in particular those devices that have been characterized as so-called electronic cigarettes, have been marketed under the tradenames BLU™; COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP® and SOUTH BEACH SMOKE™. In some of these electronic smoking articles, when the user inhales on the electronic smoking article, aerosol precursor material is 'pulled' from the reservoir into a vaporizing chamber using gravity and capillary in the wick. The aerosol precursor material is either adsorbed or resting on the electronic smoking article's heating apparatus and heated until it becomes vapor. The vapor is drawn away from the heated region of the device, where it subsequently cools and condenses into a high number density, generally sub-micron aerosol whereupon it then exits the device. The wick material can include any combination of silica, organic cotton, cellucotton rayon fibers, stainless steel, fiberglass, ceramic, and other materials with similar properties.

Just as combustible cigarettes must be tested to determine the levels of various compounds present in the smoke inhaled by a user, E-cigarettes must also be tested to determine the levels of various compounds present in the vapor inhaled by a user. A conventional testing method includes connecting the e-cigarette to a puffing machine that simulates a user inhaling. The vapor from the simulated inhalation passes through a filter, and the filter captures the compounds present in the vapor for subsequent testing. A common filter used in this application is a Cambridge pad filter. The filter is analyzed to determine the compound levels present in the vapor that a user would inhale.

Conventional testing systems are designed to accommodate a combustible cigarette or e-cigarette that has a mouthpiece with a circular cross-section. However, some e-cigarettes do not have a mouthpiece with a circular cross-section. When connecting a mouthpiece with a non-circular cross-section to a conventional testing system, additional components are needed to couple the mouthpiece with a non-circular cross-section of the e-cigarette to the connectors with circular cross-sections on the conventional testing system. These additional components create areas that can capture liquid or vapor during testing and prevent the liquid or vapor from reaching the filter, thus compromising the test results.

SUMMARY

One embodiment relates to a system for testing a product. In this embodiment, the system includes a filter pad holder comprising a body portion and a neck portion, and an adaptor coupled to the neck portion of the filter pad holder. The adaptor of this embodiment includes a nose configured to receive the neck portion and an adaptor body coupled to the adaptor nose. In this embodiment, an adaptor port is defined by the adaptor nose and extends from an outer surface of the adaptor nose to an interior portion of the adaptor. An opening of this embodiment is defined by the adaptor body and the adaptor nose, the opening extending through the adaptor body and the adaptor nose and configured to receive the neck portion. A sealing member of this embodiment is configured to be received by the adaptor and the filter pad holder. In this embodiment, the sealing member includes a sealing member nose configured to be received by the neck portion, and a sealing member body coupled to the sealing member nose and configured to be received by the opening. The sealing member body, in this embodiment, defines an orifice, the orifice extending through the sealing member body. At least one sealing surface of this embodiment is located within the orifice, the at least one sealing surface configured to create a seal with a mouthpiece of the product, the mouthpiece possessing a non-circular cross-section. In this embodiments, an outlet is defined by the sealing member nose, the outlet extending from the orifice through the sealing member nose and in fluid communication with the product. A sealing member port of this embodiment is defined by the sealing member nose and extends from an outer surface of the sealing member nose to the outlet. The sealing member port of this embodiments is in fluid communication with the adaptor port.

Another embodiment relates to a system for testing a product. The system, in this embodiment, includes a filter pad holder comprising a body portion and a neck portion, and an adaptor coupled to the neck portion of the filter pad holder. The adaptor of this embodiment includes an adaptor nose configured to receive the neck portion and an adaptor body coupled to the adaptor nose. In this embodiment, an adaptor port is defined by the adaptor nose and extends from an outer surface of the adaptor nose to an interior portion of the adaptor. An opening, in this embodiment, is defined by the adaptor body and the adaptor nose, the opening extending through the adaptor body and the adaptor nose and configured to receive the neck portion. A sealing member of this embodiment is configured to be received by the adaptor and the filter pad holder. The sealing member, in this embodiment, includes a sealing member nose configured to be received by the neck portion, and a sealing member body coupled to the sealing member nose and configured to be received by the opening. The sealing member body of this embodiment defines an orifice, the orifice extending through the sealing member body. In this embodiment, a slot extends from the orifice partially through the sealing member body. At least one sealing surface, in this embodiment, is within the orifice, the at least one sealing surface configured to create a seal with a mouthpiece of the product, the mouthpiece possessing a non-circular cross-section. In this embodiment, an outlet is defined by the sealing member nose, the outlet extending from the orifice through the sealing member nose and in fluid communication with the product. A sealing member port of this embodiment is defined by the sealing member nose and extends from an outer surface of the sealing member nose to the outlet. The sealing member port, in this embodiment, is in fluid communication with the adaptor port via a gap defined by an inner surface of the adaptor nose and the outer surface of the adaptor port.

Still another embodiment relates to a method for testing a product with a mouthpiece possessing a non-circular cross-section. In this embodiment, the method includes providing a system for testing a product. The system of this embodiment includes a filter pad holder comprising a body portion and a neck portion. An adaptor, in this embodiment, is coupled to the neck portion of the filter pad holder, and the adaptor includes an adaptor nose configured to receive the neck portion and an adaptor body coupled to the adaptor nose. In this embodiment, an adaptor port is defined by the adaptor nose and extends from an outer surface of the adaptor nose to an interior portion of the adaptor. An opening of this embodiment is defined by the adaptor body, the opening extending through the adaptor body and the adaptor nose and configured to receive the neck portion. A sealing member, in this embodiment, is configured to be received by the adaptor and the filter pad holder, the sealing member comprising a sealing member nose configured to be received by the neck portion and a sealing member body coupled to the sealing member nose and configured to be received by the opening. In this embodiment, the sealing member body defines an orifice, the orifice extending through the sealing member body. At least one sealing surface of this embodiment is within the orifice, the at least one sealing surface configured to create a seal with the mouthpiece of the product. An outlet of this embodiment is defined by the sealing member nose, the outlet extending from the orifice through the sealing member nose and in fluid communication with the product. In this embodiment, a sealing member port is defined by the sealing member nose and extends from an outer surface of the sealing member nose to the outlet. The sealing member port in fluid communication with the adaptor port. The method of this embodiment further includes inserting the mouthpiece into the orifice such that a seal is created between the mouthpiece and the at least one sealing surface and suspending the product from the system such that the product is prevented from falling by the at least one sealing surface. The method of this embodiment includes coupling the system to a puffing machine, the puffing machine configured to simulate use of the product, and initiating the puffing machine to cause the product to create fluid, wherein the outlet is configured to direct fluid from the product to the filter pad holder.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are therefore not to be considered limiting of its scope, the disclosure will be described with additional specificity and detail through use of the accompanying drawings. Exemplary embodiments of the present application will now be described, by way of example only, with reference to the accompanying drawings, which are not necessarily drawn to scale, and wherein:

FIGS. 4A-4C are various perspective and cross-sectional views of a test assembly for testing a vapor product, according to a particular embodiment.

FIGS. 5A-5C are various perspective and cross-sectional views of a test assembly for testing a vapor product, according to a particular embodiment.

DETAILED DESCRIPTION

Referring generally to the figures, a system for testing a vapor product is shown. An example of a vapor product is an e-cigarette. An e-cigarette producer may desire to test a non-cylindrical e-cigarette product to determine the performance of the e-cigarette by testing the vapor drawn from the mouthpiece of the non-cylindrical e-cigarette. As described herein, a non-cylindrical e-cigarette product refers to an e-cigarette that includes a mouthpiece that is not circular in cross-section. As described herein, a cylindrical e-cigarette product refers to an e-cigarette that includes a mouthpiece that is circular in cross-section. To test the non-cylindrical e-cigarette in a conventional testing system, the producer must include additional components such that the non-cylindrical e-cigarette can be operatively connected to the conventional testing system that is designed to accommodate a cylindrical product. Because additional components are included, the flow of vapor from the mouthpiece to the filter pad included with the testing system may be compromised, resulting in undesirable testing outcomes.

A testing system according to various embodiments comprises a sealing member and an adaptor. The adaptor is operatively coupled to the filter pad holder and to the sealing member. The sealing member is operatively coupled to the adaptor and the non-cylindrical e-cigarette, and is fluidly coupled to the filter pad holder. The sealing member is configured to accommodate a non-cylindrical e-cigarette such that no additional components are needed to provide a secure connection. The sealing member provides an outlet that is configured to direct vapor from the non-cylindrical e-cigarette to the filter pad holder without compromising the flow of vapor.

Figure 1A:
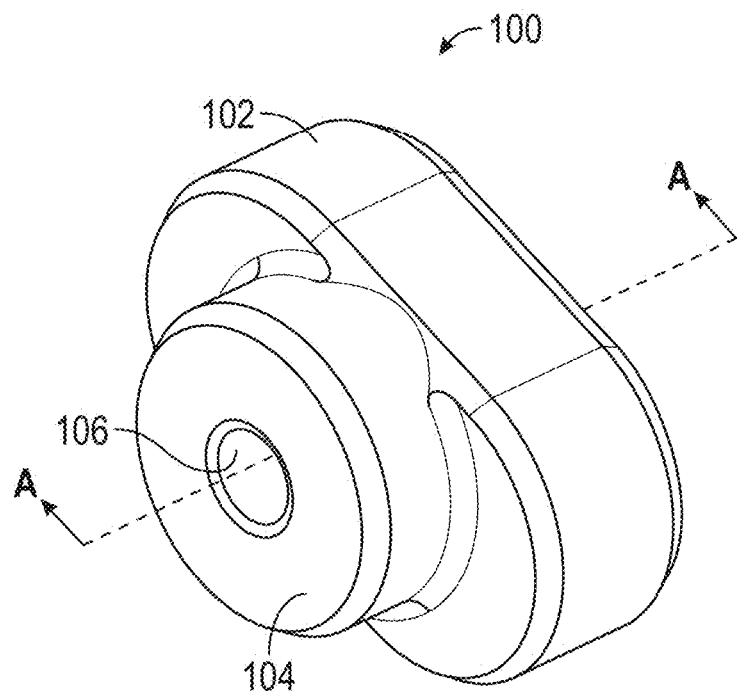
FIGS. 1A-1B are perspective views of a sealing member for use with a system for testing a vapor product, according to a particular embodiment.
Figure 1B:
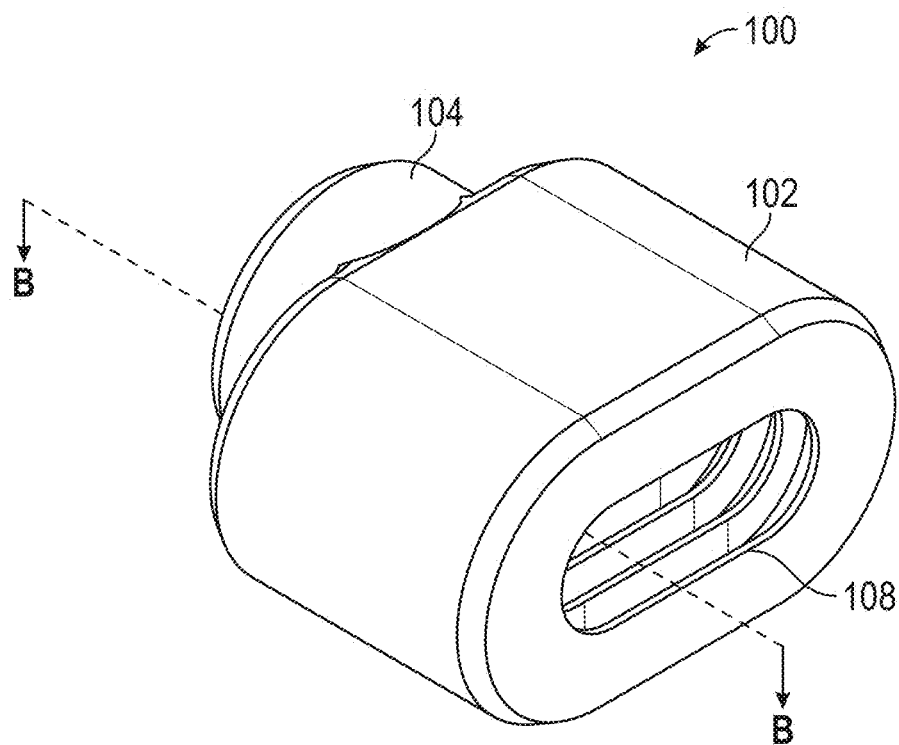

Referring now to FIGS. 1A-1B, perspective views of a sealing member 100 for use with a system for testing a vapor product are shown, according to a particular embodiment. The sealing member 100 includes a sealing member body 102, a sealing member nose 104, an outlet 106, and an orifice 108. The sealing member 100 can be manufactured from a resilient material (e.g., silicone, rubber, or other resilient materials) that is capable of being elastically deformed and returning to its pre-deformed shape. In some embodiments, the sealing member can be manufactured from a medical-grade resilient material. As shown, the sealing member 100 is a single component, however in some embodiments the sealing member 100 can be constructed from multiple components.

The sealing member body 102 has a non-circular cross-section and is configured to couple with an adaptor for a filter pad holder, which will be further described with reference to FIG. 3. As shown, the cross-section of the sealing member body 102 has a "racetrack" shape, with "racetrack" referring to two curved portions positioned opposite each other with straight sections between the curved portions. The "racetrack" shape can also be referred to as a "stadium" shape, a discorectangle, an obround shape, and a "compound radius". In some arrangements where the adaptor exhibits other shapes, the cross-section of the sealing member body 102 can be shaped appropriately (e.g., rectangular, elliptical, oval, square, or other shapes that do not have a circular cross-section) to couple with the adaptor.

The orifice 108 extends through the sealing member body 102 such that the orifice 108 is in fluid communication with the outlet 106. The orifice 108 is sized and configured to receive a non-cylindrical mouthpiece of an e-cigarette. As shown, the orifice 108 has a racetrack shape. However, in some embodiments the orifice 108 can exhibit other shapes (e.g., rectangular, square, or other shapes that do not have a circular cross-section) to match the shape of the non-cylindrical mouthpiece. In some implementations, the sealing member body 102 and the orifice 108 can be the same shape. In some implementations, the sealing member body 102 and the orifice 108 can be different shapes.

The sealing member nose 104 extends from the sealing member body 102 and has a cross-section that is substantially circular, in some arrangements. The sealing member nose 104 is configured to couple with the filter pad holder. In embodiments where the filter pad holder exhibits a mating surface that is not substantially circular, the sealing member nose 104 can be shaped as needed such that the sealing member nose 104 couples appropriately with the adaptor.

The outlet 106 extends from the orifice 108 through the sealing member nose 104 such that the outlet 106 is in fluid communication with the orifice 108. The outlet 106 is sized and configured to receive vapor from a vapor product (e.g., an e-cigarette) and direct the vapor through the outlet 106 and toward a filter pad. The shape of the outlet 106 will be further described with reference to FIGS. 1C-1D.

Figure 1C:
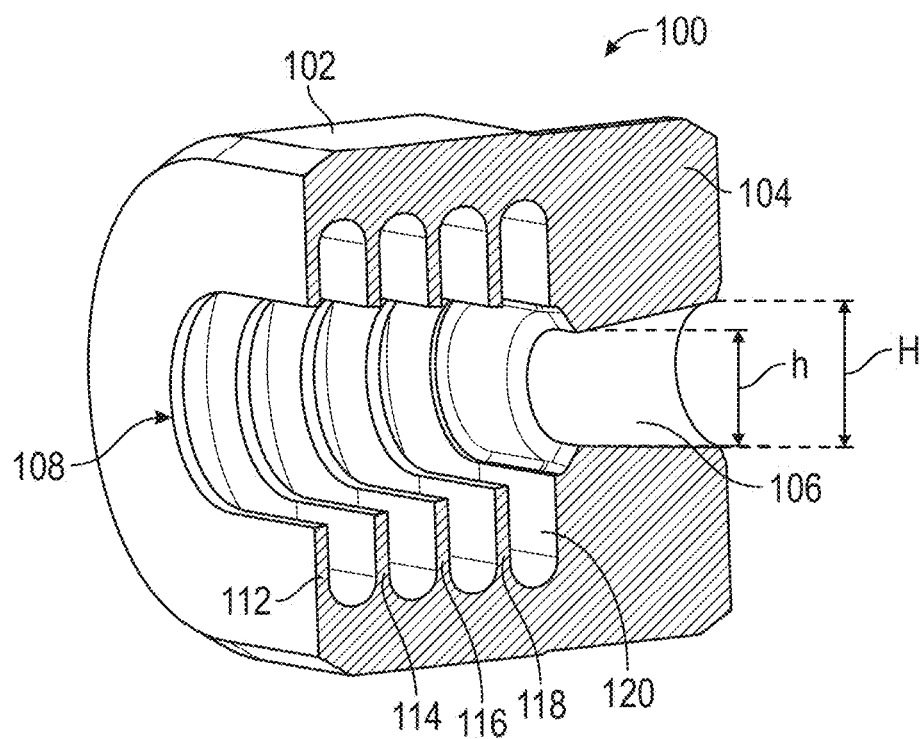
FIGS. 1C-1D are cross sectional views of the sealing member of FIG. 1.
Figure 1D:
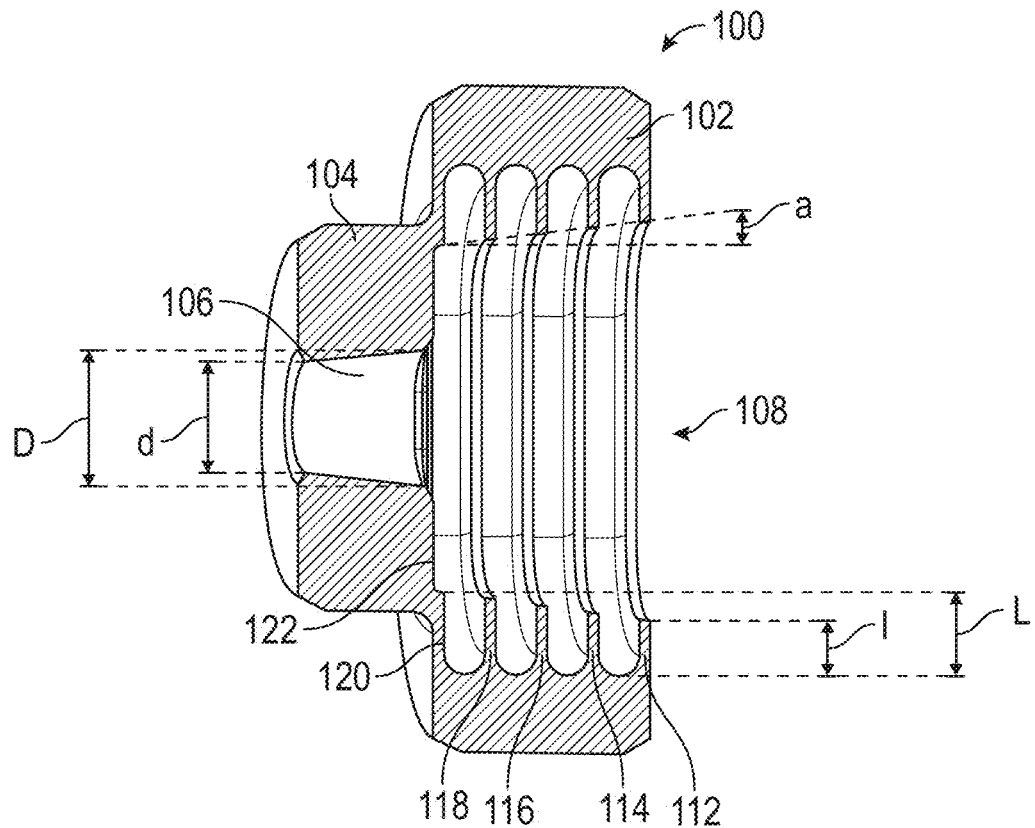

FIG. 1C is a cross-sectional view from section A-A of the sealing member 100 of FIG. 1A. FIG. 1D is a cross-sectional view from section B-B of the sealing member 100 of FIG. 1B. As shown, the outlet 108 includes a first sealing surface 112, a second sealing surface 114, a third sealing surface 116, a fourth sealing surface 118, a fifth sealing surface 120, and a sealing base 122. The first sealing surface 112, second sealing surface 114, third sealing surface 116, fourth sealing surface 118, and fifth sealing surface 120 (referred to herein as "the sealing surfaces 112-120") can be formed integrally with the orifice 108. The sealing surfaces 112-120 are configured to contact a non-cylindrical mouthpiece of a vapor product such that a seal is created between the sealing surfaces 112-120 and the non-cylindrical mouthpiece. As such, the shape of the sealing surfaces 112-120 can be modified as needed to match the shape of the non-cylindrical mouthpiece being used. The sealing surfaces 112-120 are flexible and resilient such that the sealing surfaces 112-120 can be deformed when a non-cylindrical mouthpiece is inserted into the orifice 108, and after the non-cylindrical mouthpiece is removed, the sealing surfaces 112-120 return to their original shapes and orientations.

In the embodiment shown in FIGS. 1C-1D, the sealing surfaces 112-120 are tapered. For example, the first sealing surface 112 protrudes into the orifice 108 by a length l and the fifth sealing surface 120 protrudes into the orifice 108 by a length L, where L is greater than l. The second sealing surface 114, the third sealing surface 116, and the fourth sealing surface 118 also protrude into the orifice 108 by constantly increasing lengths between l and L such that the sealing surfaces 112-120 create a tapered seal (e.g., tapered at an angle α) to match the taper of the mouthpiece of the vapor product being tested. In other implementations where the mouthpiece of the tapered product is shaped differently, the sealing surfaces 112-120 can be designed and manufactured to match the shape of the mouthpiece to create a seal.

The sealing base 122 provides a surface for an end of the non-cylindrical mouthpiece to contact when the non-cylindrical mouthpiece is inserted into the orifice 108. The sealing base 122 is flexible and resilient such that the sealing base 122 can be deformed when the non-cylindrical mouthpiece contacts the sealing base 122, and after the non-cylindrical mouthpiece is removed from the sealing base 122, the sealing base 122 can return to its original shape.

The outlet 106 extends from the sealing base 122 through the sealing member nose 104 such that the outlet 106 is in fluid communication with the orifice 108. The outlet 106 is sized and configured to receive vapor from a non-cylindrical vapor product and direct the vapor to a filter pad. In the embodiment shown in FIG. 1C, the outlet 106 has a frustoconical shape where the larger portion of the frustoconical shape, denoted as H, is located at the tip of the sealing member nose 104 and the smaller portion of the frustoconical shape, denoted as h, is located near the sealing base 122. In the arrangement shown in FIG. 1D, the outlet 106 has a frustoconical shape where the larger portion of the frustoconical shape, denoted as D, is located near the sealing base 122 and the smaller portion of the frustoconical shape, denoted as d, is located at the tip of the sealing member nose 104. In some implementations, the outlet 106 can be a variety of shapes other than frustoconical configured to direct vapor from the non-cylindrical product to the filter pad.

Figure 2:
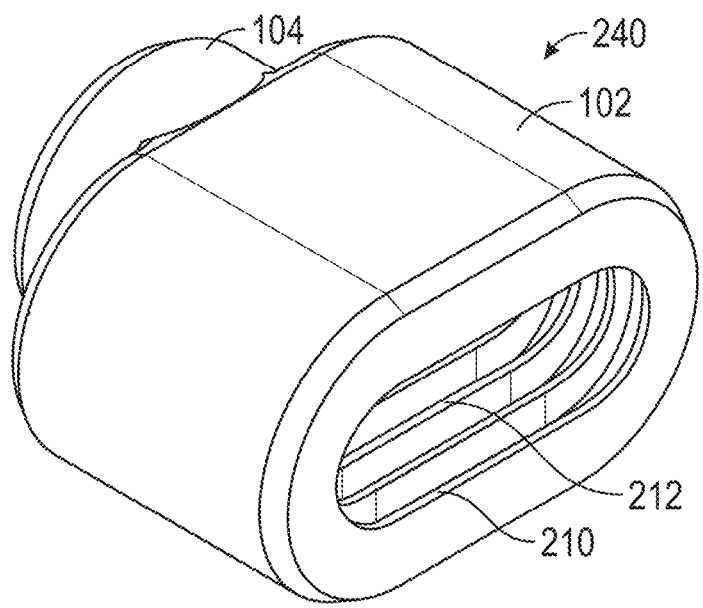
FIG. 2 is a perspective view of a sealing member for use with a system for testing a vapor product, according to particular embodiments.

FIG. 2 is a perspective view of a sealing member 240 for use with a system for testing a vapor product. The sealing member 240 includes an orifice 210 and sealing surfaces 212 configured to receive a non-cylindrical vapor product. The sealing member 240 further includes the sealing member body 102, the sealing member nose 104, and the outlet 106 (not shown). In some embodiments, the sealing member 240 can include a slot (not shown) that extends from the orifice 210 and partially through the sealing member body 102. The function of the slot will be further described with reference to FIG. 5. Because various dimensions of non-cylindrical vapor products can differ between products and manufacturers, the various dimensions of the sealing member 240 can be modified to accommodate non-cylindrical vapor products with different dimensions. This provides for flexibility in test system setup, as many different sealing members can be created for various sizes of non-cylindrical products while maintaining compatibility with an adaptor configured to receive the sealing member body 102 and the sealing member nose 104.

Figure 3:
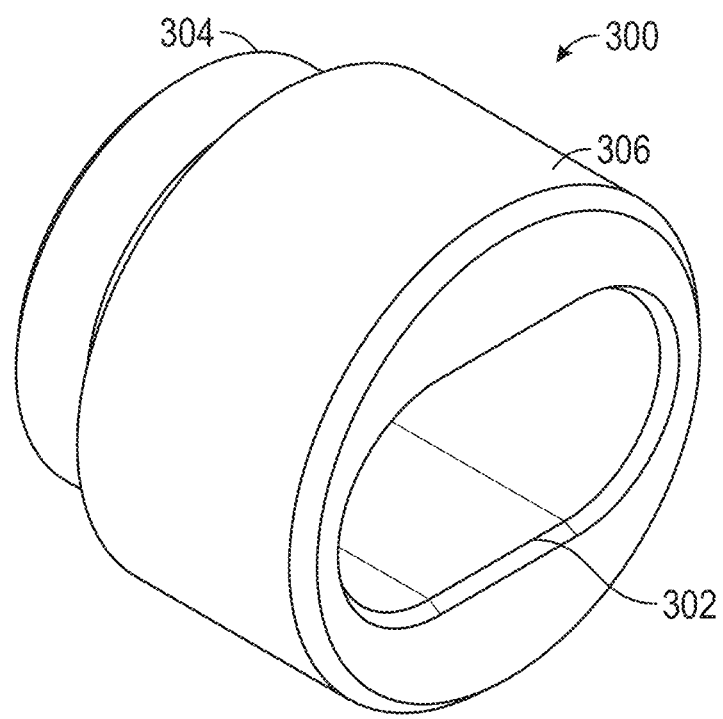
FIG. 3 is a perspective view of an adaptor for use with a system for testing a vapor product, according to a particular embodiment.

FIG. 3 is a perspective view of an adaptor 300 for use with a system for testing a vapor product, according to a particular embodiment. The adaptor 300 includes an opening 302, an adaptor nose 304, and an adaptor body 306. The adaptor 300 can be manufactured from a wide variety of plastic materials (e.g., polycarbonate, nylon, or any other suitable plastic material) or metal materials (e.g., stainless steel, aluminum, or any other suitable metal material). In some embodiments, the sealing member can be manufactured from medical-grade plastic or metal materials. The adaptor 300 can be molded or machined as a single component. The adaptor 300 can also be manufactured as multiple, separate components that are subsequently coupled to each other to form an assembly.

In the embodiment shown in FIG. 3, the adaptor body 306 is shown as having a circular cross-section. However, in some embodiments the adaptor body 306 can include a wide variety of cross-sectional shapes (e.g., elliptical, rectangular, or any other suitable cross-sectional shape) that provide the desired result. The adaptor body 306 includes the opening 302. The opening 302 extends through the adaptor body 306 and is configured to receive the sealing member body 102 of FIGS. 1-2.

The adaptor nose 304 extends from the adaptor body 306, and the opening 302 extends from the adaptor body 306 through the adaptor nose 304. The opening 302 is also in communication with the filter pad holder. The interaction between the adaptor nose 304 and the filter pad holder will be further described with reference to FIGS. 4-5.

Figure 4C:
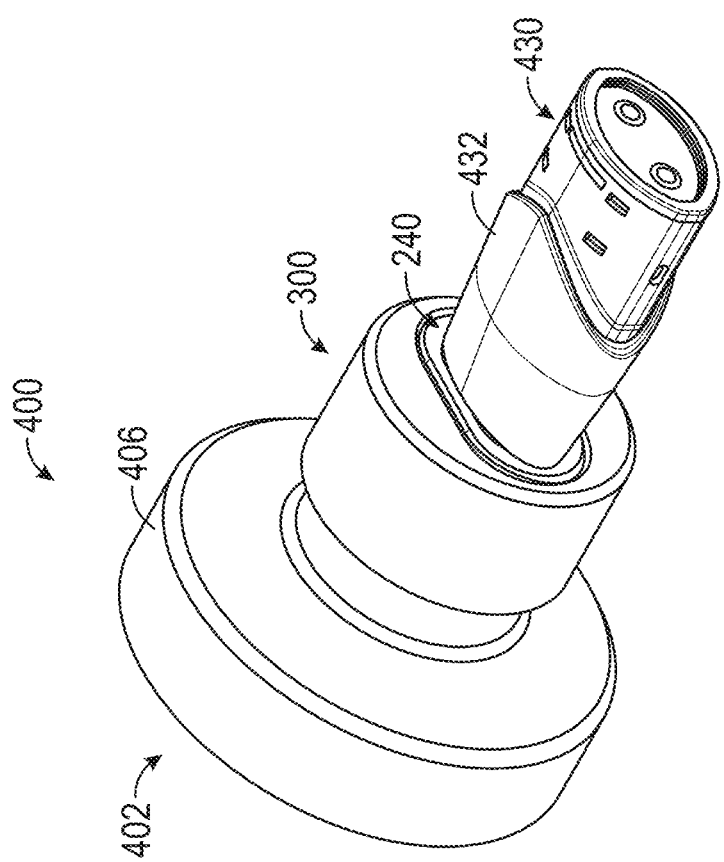

FIGS. 4A-4C are various perspective and cross-sectional views of a test assembly 400 for testing a vapor product, according to a particular embodiment. The test assembly 400 can be used to test the vapor from a non-cylindrical vapor product. The test assembly 400 includes a filter pad holder 402, a vapor product 430, the adaptor 300, and the sealing member 240.

The filter pad holder 402 includes a body 406, a neck 408, a filter pad 404, a first sealing component 410, an inlet 414, and a recess 416. The filter pad holder 402 can be manufactured from plastics (e.g., ABS, polyethylene, polycarbonate, or other suitable plastics) metals (e.g., stainless steel, aluminum, or other suitable metals), or any other suitable material. The filter pad holder 402 is configured to couple with the sealing member 240 and the adaptor 300 to create the test assembly 400.

The filter pad 404 is secured in the body 406 and is configured to absorb vapor from the vapor product 430. An example of the filter pad 404 is a Cambridge filter pad. As shown, the filter pad 404 and the body 406 have circular cross-sections. However, in some embodiments the filter pad 404 and the body 406 can have other cross-sectional shapes. The neck 408 extends from the body 406 and includes a recess 416 extending at least partially through the neck 408. The recess 416 is sized and configured to receive the sealing member nose 104 of the sealing member 220. The inlet 414 is an opening extending through the recess 416 and is in fluid communication with the outlet 106 and the filter pad 404.

The neck 408 includes a first sealing component 410 that is configured to create a seal between the neck 408 and the adaptor 300. The first sealing component 410 can be any resilient component that can create a seal between surfaces. For example, the first sealing component 410 can be an o-ring, a gasket, or any other type of sealing component. As shown, the first sealing component 410 has a circular cross-section; however, in some embodiments the first sealing component 410 can have a wide variety of cross-sections (e.g., square, rectangular, elliptical, or any other shape).

The adaptor 300 includes a second sealing component 412 that is located in the adaptor nose 304 and is configured to create a seal between the adaptor nose 304 and the neck 408. The second sealing component 412 can be any resilient component that can create a seal between surfaces. For example, the second sealing component 412 can be an o-ring, a gasket, or any other type of sealing component. As shown, the second sealing component 412 has a circular cross-section; however, in some embodiments the second sealing component 412 can have a wide variety of cross-sections (e.g., square, rectangular, elliptical, or any other shape).

The vapor product 430 can be any type of vapor product (e.g., an e-cigarette) and includes a mouthpiece 432. The vapor product 430 is configured to heat a liquid enclosed in the vapor product 430 when an inhalation force is applied to the mouthpiece 432. The inhalation force can be applied by a user or by a test assembly such as the test assembly 400. When the inhalation force is applied, the liquid is rapidly heated and a vapor is created. The vapor is drawn through the mouthpiece 432 by the inhalation force. As shown, the mouthpiece 432 has a racetrack cross-section. However, in some arrangements the mouthpiece 432 can have other cross-sectional shapes (e.g., rectangular, square, or other non-circular shapes).

In operation, and with reference to FIGS. 1-5, the test assembly 400 is assembled by coupling the filter pad holder 402 and the adaptor 300. When the neck 408 of the filter pad holder 402 is inserted into the adaptor nose 304 of the adaptor 300, the first sealing component 410 and the second sealing component 412 create seals between the filter pad holder 402 and the adaptor 300 to prevent vapor from escaping between the two components.

A sealing member 220 is selected based on the vapor product to be tested. In the embodiment where the vapor product 430 is selected to be tested, the sealing member 240 is selected because the sealing member 240 is designed to be coupled to the vapor product 430. The sealing member nose 104 of the sealing member 240 is inserted into the adaptor 300 until the sealing base 122 contacts the adaptor 300.

The mouthpiece 432 of the vapor product 430 is inserted into the orifice 108 and engages with the sealing surfaces 112-120 such that a seal is created between the sealing surfaces 112-120 and the mouthpiece 432 that prevents vapor from escaping between the mouthpiece 432 and the sealing member 220.

The test assembly 400 is positioned vertically such that the filter pad holder 402 is above the vapor product 430. Positioning the test assembly 400 in this manner allows vapor from the vapor product 430 to rise toward the filter pad 404 during the test. Because the test assembly 400 is positioned vertically, the sealing surfaces 112-120 are strong enough to hold the mouthpiece 432 stationary and suspend the vapor product 430 in a vertical position to prevent the vapor product 430 from slipping and/or falling from the test assembly 400.

The filter pad holder 402 is coupled to a puffing machine (not shown) that simulates inhalation/exhalation cycles such that vapor is drawn from the vapor product 430. For example, when the puffing machine runs an inhalation cycle, the puffing machine imparts a vacuum to the filter pad holder 402 to simulate a user inhaling. The vacuum is imparted through the filter pad 404, the inlet 414, and the outlet 106 to reach the mouthpiece 432. When the vapor product 430 senses the vacuum on the mouthpiece 432, the liquid in the vapor product 430 is heated to create vapor. The vapor is drawn by the vacuum through the outlet 106 and the inlet 414 such that the vapor reaches the filter pad 404. The frustoconical shape of the outlet 106 helps direct the vapor away from the mouthpiece 432 and toward the filter pad 404. The filter pad 404 captures the vapor during the testing process. After the testing process is complete, the filter pad 404 is removed and tested to determine the components of the vapor.

Figure 5A:
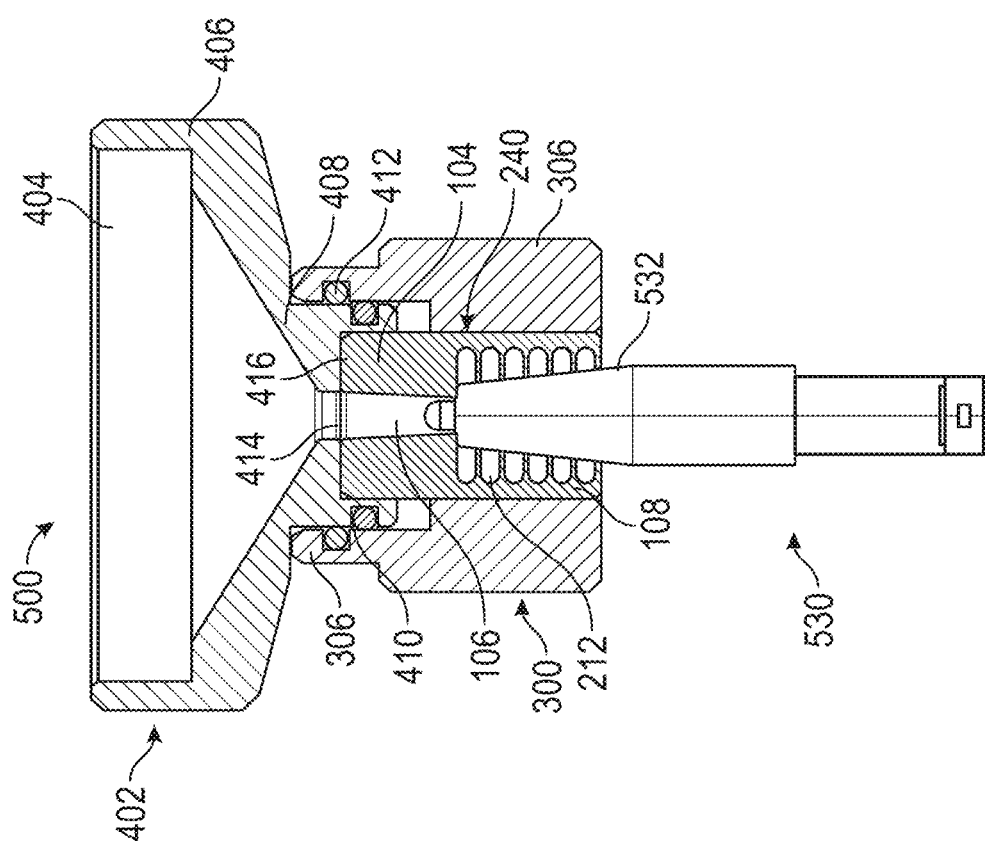

FIGS. 5A-5C are various perspective and cross-sectional views of a test assembly 500 for testing a vapor product, according to a particular embodiment. The test assembly 500 is substantially similar to the test assembly 400, however the test assembly 500 is shown testing a vapor product 530 with a mouthpiece 532. Because the mouthpiece 532 is shaped differently than the mouthpiece 432 from FIG. 4, the embodiment of the sealing member 240 that includes a slot is used because the slot is designed to fit with the mouthpiece 532.

As shown, the sealing member 240 includes a slot 510 located in the sealing member nose 104. The slot 510 is a recess extending partially into the sealing member nose 104 such that the sealing member nose 104 does not interfere with the pressure sensor in the vapor product 530. In some embodiments, the pressure sensor on the vapor product 530 is situated adjacent to the mouthpiece 532 to detect the vacuum and initiate the heating element to heat the liquid. If the pressure sensor is blocked by the sealing member 240, the vapor product 530 would not sense the vacuum imparted by the puffing machine and therefore would not heat the liquid to create the vapor. With the slot 510 preventing the pressure sensor from being blocked, the test assembly 500 operates in the same manner as the test assembly 400.

Figure 6:
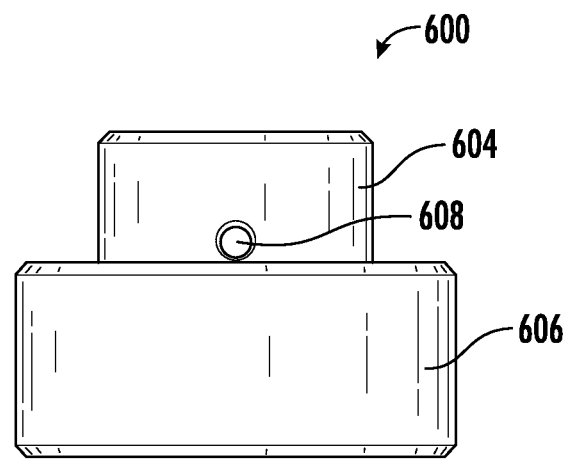
FIG. 6 is a side view of an adaptor with a thermal port, according to a particular embodiment.

FIG. 6 is a side view of an adaptor 600 with an adaptor port 608, according to a particular embodiment. The adaptor 600 of the illustrated embodiment is similar in several respects to the adaptor 300, except for the addition of the adaptor port 608. Accordingly, the adaptor nose 604 and the adaptor body 606 of this embodiment are similar to the adaptor nose 304 and the adaptor body 306, respectively, of FIG. 3. The adaptor nose 604 of the illustrated embodiment defines an adaptor port 608 that extends through a portion of the adaptor nose 604 to reach an interior portion of the adaptor 600. The adaptor port 608 of this embodiment is configured to receive one or more sensors to measure and/or analyze various characteristics of a vapor product being tested using the adaptor 600. In some embodiments, the sensors can include one or more of a thermocouple, a pressure sensor, a flow sensor, or any other type of sensor configured to detect one or more characteristics associated with testing a vapor product. For example, in some embodiments, the sensor includes a thermocouple or thermal probe configured to detect an exit temperature of a vapor product (e.g., the temperature of the vapor product as the vapor exits the vapor product).

In some embodiments, the one or more sensors are sized such that the one or more sensors creates a seal with an inner surface of the adaptor port 608 to prevent air and/or vapor from escaping from the adaptor port 608. In some embodiments, a seal is created between the one or more sensors and the inner surface of the adaptor port 608 with an adhesive material. For example, in some embodiments a silicone adhesive may be used to affix the one or more sensors within the adaptor port 608 and fill any air gaps between the one or more sensors and the inner surface of the adaptor port 608 to create a seal that prevents air and/or vapor from escaping from the adaptor port 608.

Figure 7:
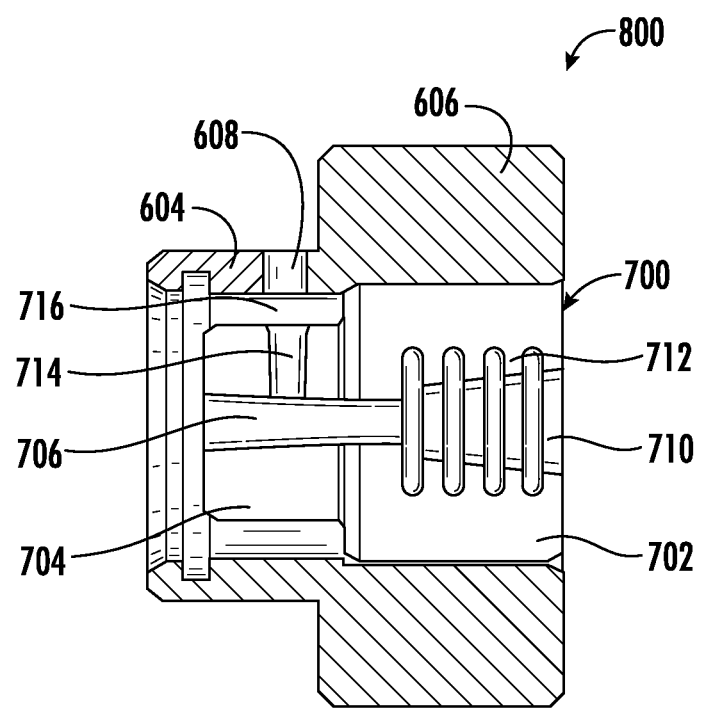
FIG. 7 is a cross-sectional view of a portion of a test assembly including the adaptor of FIG. 6, according to a particular embodiment.

FIG. 7 is a cross-sectional view of a portion of a test assembly 800 including the adaptor of FIG. 6, according to a particular embodiment. For example, the test assembly 800 of the illustrated embodiment shows the adaptor 600 in communication with a sealing member 700. The sealing member 700 of the illustrated embodiment is similar to the sealing member 100 and the sealing member 240, with the only difference being that the sealing member 700 includes a sealing member port 714. Accordingly, the sealing member body 702, the sealing member nose 704, the outlet 706, the orifice 708, and the sealing surfaces 712 of this embodiment are similar to corresponding features of the sealing member 100 and the sealing member 240, respectively.

In some embodiments, the sealing member port 714 extends through a portion of the sealing member 700 from an outer surface of the sealing member port 714 to the outlet 706. Accordingly, the sealing member port 714 of this embodiment is in fluid communication with the outlet 706. The sealing member port 714 of the illustrated embodiment is configured to receive the one or more sensors that extend through the adaptor port 608 such that the one or more sensors can be positioned within the flow of the vapor product as the vapor product flows through the outlet 706. For example, in some embodiments, the one or more sensors can be positioned within a gap 716 that extends between the sealing member 700 and the adaptor 600, where the gap 716 is defined by an inner surface of the adaptor nose 604 and an outer surface of the sealing member nose 704. In some embodiments, positioning the one or more sensors within the gap 716 allows vapor to flow unencumbered through the outlet 706 such that particulate matter to be measured by a filter pad (e.g. the filter pad 404) is not disrupted by the presence of the one or more sensors.

In operation, in some embodiments a manufacturer may desire to determine a characteristic of vapor as vapor exits a vapor product. Based on the measured characteristic, the manufacturer may modify the vapor product to change the characteristic. For example, in some embodiments, based on a measured exit temperature, the manufacturer may modify the vapor product to increase or decrease the exit temperature. To measure the exit temperature in the illustrated embodiments, the manufacturer connects a vapor product to the test assembly 800 to measure both the particulate in the vapor and the exit temperature of the vapor. When the test is initiated, a puffing machine draws vapor from the vapor product in this embodiment. As the vapor flows through the outlet 706 of the illustrated embodiment, a portion of the vapor is directed through the sealing member port 714 such that the vapor contacts the one or more sensors positioned within the gap 716 or the adaptor port 608. In some embodiments, the remainder of the vapor flows to the filter pad (not shown) to measure an amount of particulate that may be present in the vapor.

The vapor products described herein have referred to heating elements and wick and coil technology to create the vapor that is drawn through the filter pad. However, the vapor products described herein can generate vapor with any suitable atomization technology including, but not limited to, heating, vibrating piezoelectric, piezomagnetic mesh, and any other technology configured to atomize liquid and generate vapor.

Embodiments described above generally reference vapor products. However, additional products with non-cylindrical mouthpieces can be encompassed by the foregoing description. Examples of products include, but are not limited to, hookah pipes, water pipes, tobacco pipes, and any other product or device where using the device or product generates a byproduct or waste product (e.g., smoke, water particles, etc.) that can be captured and measured.

As utilized herein, the term "substantially," and similar terms are intended to have a broad meaning in harmony with the common and accepted usage by those of ordinary skill in the art to which the subject matter of this disclosure pertains. It should be understood by those of ordinary skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

Although only a few embodiments have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter described herein. For example, elements shown as integrally formed may be constructed of multiple components or elements, the position of elements may be reversed or otherwise varied, and the nature or number of discrete elements or positions may be altered or varied. The order or sequence of any method processes may be varied or re-sequenced according to alternative embodiments. Other substitutions, modifications, changes, and omissions may also be made in the design, operating conditions and arrangement of the various exemplary embodiments without departing from the scope of the present invention.

What is claimed is:

1. A system for testing a product, comprising:
a filter pad holder;
an adaptor coupled to the filter pad holder, the adaptor defining an opening extending therethrough and configured to engage a portion of the filter pad holder;
a sealing member configured to engage the adaptor and the filter pad holder, the sealing member comprising:
a sealing member nose configured to engage the filter pad holder;
a sealing member body coupled to the sealing member nose and configured to engage the opening, the sealing member body defining an orifice, the orifice extending through the sealing member body;
at least one sealing surface within the orifice, the at least one sealing surface configured to create a seal with a mouthpiece of the product;
an outlet defined by the sealing member nose, the outlet extending from the orifice through the sealing member nose and in fluid communication with the product; and
a sealing member port defined by the sealing member nose, the sealing member port extending from an outer surface of the sealing member nose to the outlet, the sealing member port in fluid communication with the adaptor.

2. The system of claim 1, wherein the filter pad holder defines an inlet extending through the filter pad holder, the inlet in fluid communication with the outlet.

3. The system of claim 2, wherein the filter pad holder includes a first sealing component, the first sealing component forming a seal with the adaptor when the first sealing component is coupled to the adaptor.

4. The system of claim 2, wherein the adaptor includes a second sealing component, the second sealing component forming a seal with the filter pad holder when the second sealing component is coupled to the filter pad holder.

5. The system of claim 2, wherein the at least one sealing surface comprises a plurality of sealing surfaces.

6. The system of claim 5, wherein the mouthpiece is tapered such that a smaller portion of the mouthpiece is adjacent to the outlet and a larger portion of the mouthpiece extends away from the outlet, the plurality of sealing surfaces configured to create a seal with the smaller portion and the larger portion.

7. The system of claim 6, wherein the at least one sealing surface is deformable so as to match the shape of the mouthpiece.

8. The system of claim 7, wherein the plurality of sealing surfaces are configured to suspend the product vertically and prevent the product from slipping out of the plurality of sealing surfaces.

9. The system of claim 1, wherein the outlet is configured to direct a portion of a byproduct from the mouthpiece to the filter pad holder and a remainder of the byproduct through the sealing member port such that a characteristic of the byproduct can be measured.

10. A system for testing a product, comprising:
a filter pad holder;
an adaptor coupled to the filter pad holder, the adaptor defining an opening extending therethrough and configured to engage a portion of the filter pad holder;
a sealing member configured to engage the adaptor and the filter pad holder, the sealing member comprising:
a sealing member nose configured to engage the filter pad holder;
a sealing member body coupled to the sealing member nose and configured to engage the opening, the sealing member body defining an orifice, the orifice extending through the sealing member body;
a slot extending from the orifice and partially through the sealing member body;
at least one sealing surface within the orifice, the at least one sealing surface configured to create a seal with a mouthpiece of the product;
an outlet defined by the sealing member nose, the outlet extending from the orifice through the sealing member nose and in fluid communication with the product; and
a sealing member port defined by the sealing member nose, the sealing member port extending from an outer surface of the sealing member nose to the outlet, the sealing member port in fluid communication with the adaptor.

11. The system of claim 10, wherein the filter pad holder defines an inlet extending through the filter pad holder, the inlet in fluid communication with the outlet.

12. The system of claim 11, wherein the filter pad holder includes a first sealing component, the first sealing component forming a seal with the adaptor when the first sealing component is coupled to the adaptor.

13. The system of claim 11, wherein the adaptor includes a second sealing component, the second sealing component forming a seal with the filter pad holder when the second sealing component is coupled to the filter pad holder.

14. The system of claim 11, wherein the at least one sealing surface comprises a plurality of sealing surfaces.

15. The system of claim 14, wherein the mouthpiece is tapered such that a smaller portion of the mouthpiece is adjacent to the outlet and a larger portion of the mouthpiece extends away from the outlet, the plurality of sealing surfaces configured to create a seal with the smaller portion and the larger portion.

16. The system of claim 15, wherein the at least one sealing surface is deformable so as to match the shape of the mouthpiece.

17. The system of claim 16, wherein the plurality of sealing surfaces are configured to suspend the product vertically and prevent the product from slipping out of the plurality of sealing surfaces.

18. The system of claim 10, wherein the outlet is configured to direct a portion of a vapor from the mouthpiece to the filter pad holder and a remainder of the vapor through the sealing member port such that a characteristic of the vapor can be measured.

19. A method for testing a product with a mouthpiece possessing a non-circular cross-section, comprising:
providing a system for testing a product, the system comprising:
a filter pad holder;
an adaptor coupled to the filter pad holder, the adaptor defining an opening extending therethrough and configured to engage a portion of the filter pad holder;
a sealing member configured to engage the adaptor and the filter pad holder, the sealing member comprising:
a sealing member nose configured to engage the filter pad holder;
a sealing member body coupled to the sealing member nose and configured to engage the opening, the sealing member body defining an orifice, the orifice extending through the sealing member body;
at least one sealing surface within the orifice, the at least one sealing surface configured to create a seal with the mouthpiece;
an outlet defined by the sealing member nose, the outlet extending from the orifice through the sealing member nose and in fluid communication with the product; and
a sealing member port defined by the sealing member nose, the sealing member port extending from an outer surface of the sealing member nose to the outlet, the sealing member port in fluid communication with the adaptor;
inserting the mouthpiece into the orifice such that a seal is created between the mouthpiece and the at least one sealing surface;
suspending the product from the system such that the product is prevented from falling by the at least one sealing surface;
coupling the system to a puffing machine, the puffing machine configured to simulate use of the product; and
initiating the puffing machine to cause the product to create a fluid, wherein the outlet is configured to direct the fluid from the product to the filter pad holder.

20. The method of claim 19, wherein the outlet possesses a frustoconical shape.

* * * * *